US00PP15083P2

(12) United States Plant Patent
Olesen et al.

(10) Patent No.: US PP15,083 P2
(45) Date of Patent: Aug. 17, 2004

(54) MINIATURE ROSE PLANT NAMED 'POULTY004'

(50) Latin Name: *Rosa hybrida*
Varietal Denomination: POULty004

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/685,668

(22) Filed: Oct. 14, 2003

(51) Int. Cl.[7] ..... A01H 5/00
(52) U.S. Cl. ..... Plt./118
(58) Field of Search ..... Plt./116, 118

*Primary Examiner*—Anne Marie Grunberg
*Assistant Examiner*—Susan B. McCormick-Ewoldt

(57) ABSTRACT

A new miniature rose plant which has abundant, orange and orange blend flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULty004'.

SUMMARY OF THE INVENTION

The present invention constitutes a new and distinct variety of miniature rose plant which originated from a controlled crossing between the female parent 'POULnil', described and illustrated in U.S. Plant Pat. No. 13,301 issued on Dec. 3, 2002, and the male parent, unnamed plant which has not been patented. The two parents were crossed and the resulting seeds were planted in a controlled environment. The new variety is named 'POULty004'.

The new rose may be distinguished from its seed parent, 'POULnil', by the following combination of characteristics:

1. After opening, outer petals of 'POULnil' on the upper surface are Red-Purple Group 62D at margins, Red Group 36D in the middle and basal zones, all with a faint overlay of Green-Yellow Group 1B to 1C. 'POULty004' surfaces of the same are Yellow-Orange Group 14D.
2. Flower buds of 'POULnil' are 26 to 28 mm in length while the same of 'POULty004' are 17 mm.
3. As a pot plant, flowers of 'POULnil' persist up to 8 days. Flowers of 'POULty004' last up to 18 days.

The new variety may be distinguished from its pollen parent, unnamed plant, created by the same inventors, by the following combination of characteristics:

1. The unnamed pollen parent has a petal count of 30 petals, while the same of 'POULty004' is 38 to 40.
2. The unnamed pollen parent has a leaf size of 29 (l) mm by 16 (w) mm where as 'POULty004' has a leaf size of 38 mm (l)×20 mm (w).
3. General tonality of an open flower of the pollen parent is Yellow Group 11B while the same of 'POULty004' is Orange Group 28C with distinct intonations of Yellow Group 12B to Yellow-Orange Group 16D.

The objective of the hybridization of this rose variety for commercial culture was to create a new and distinct variety with unique qualities, such as:

1. Uniform and abundant orange blend flowers;
2. Vigorous and very compact growth;

3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULty004' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULty004' was selected by the inventors as a single plant from the progeny of the hybridization in 1999.

Asexual reproduction of 'POULty004' by cuttings and traditional budding was first done by L. Pernille and Mogens N. Olesen in their nursery in Fredensborg, Denmark in June of 2000. This initial and other subsequent propagations conducted in controlled environments have demonstrated that the characteristics of 'POULty004' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULty004'. Specifically illustrated in FIG. 1:

FIG. 1.1; Open flower viewed from above, stem showing branching and the attachment of leaves and peduncle;

FIG. 1.2; Closed flower bud, various stages of a partially opened bud;

FIG. 1.3; Flower petals, detached;

FIG. 1.4; Sepals, receptacle, and peduncle;

FIG. 1.5; Mature Leaves detached, juvenile leaves attached to stem, juvenile stem with thorns;

FIG. 1.6; Bare stem exhibiting thorns.

DETAILED DESCRIPTION OF THE VARIETY

The following is a description of 'POULty004', as observed in its growth in a field nursery in Jackson County, Oreg. Observed plants are 10 months of age. Color references are made using The Royal Horticultural Society (London, England) Colour Chart, 1995, except where common terms of color are used.

For a comparison, several physical characteristics of the rose variety 'POULberty', a rose variety from the same inventors described and illustrated in U.S. Plant Pat. No. 13,103 issued on Oct. 22, 2002 are compared to 'POULty004' in Chart 1.

CHART 1

| | 'POULty0044' | 'POULberty' |
|---|---|---|
| Petal Color: outermost petals, inner side. | Yellow-Orange Group 14D. | Yellow Group 11D with marginal intonations of Yellow Group 12A to 12B. |
| Bud Color: as sepals unfold | Blend of Orange-Red Group 33B to Orange-Red Group 34C. Also distinctly present is the color Yellow Group 11B. | Orange Group 29C. |
| General Tonality | On open flower Orange Group 28C with distinct intonations of Yellow Group 12B to Yellow-Orange Group 16D. | Yellow-Orange Group 18C to 18D; guard petals Yellow-Orange Group 23D. |

Parents:

*Female.*—'POULnil'.

*Male.*—Un-named Plant.

FLOWER AND FLOWER BUD

Blooming habit: Continuous.

Flower bud:

*Size.*—Upon opening, 17 mm in length from base of receptacle to end of bud. With the foliaceous appendages, flower bud is 30 mm in length. 9 mm in diameter.

*Bud form.*—Pointed ovoid with broad base.

*Bud color.*—As sepals unfold, the flower bud is a blend of Orange-Red Group 33B to Orange-Red Group 34C. Also distinctly present is the color Yellow Group 11B. After the sepals unfold and the flower begins to open, the flower bud is Orange Group 24C with distinct intonations of Yellow Group 8C.

*Sepals.*—Upper Surface: Color: Yellow-Green Group 146B. Occasional anthocyanin observed, the color of Greyed-Red Group 178B. Texture: Varying from smooth at apecies to slightly pubescent towards the mid section and base. Lower Surface: Color: Yellow Green Group 146C with anthocyanin the color of Greyed-Red Group 178B. Texture: Smooth. Stipitate glands observed in medium quantity. Shape: General shape is subulate. Sepal apex is cirrhose with strong foliaceous extensions on 3 of the 5 sepals. Base is flat at union with receptacle. Size: 23 mm long by 4 mm wide. Foliaceous extensions are 4 mm in length.

*Receptacle.*—Surface Texture: Smooth and glaucous. Shape: Urn-shaped. Size: 5 mm in length by 6 mm wide. Color: Yellow Green Group 144A. Anthocyanin: Greyed-Red Group 181A.

*Peduncle.*—Surface: Smooth. Length: 22 mm average length. Color: Yellow Green Group 144A. On plants grown under high light conditions, peduncle may exhibit intonations of Greyed-Red Group 181A. Strength: Upright, rigid.

*Borne.*—Singly.

Flower bloom:

*Fragrance.*—Light floral.

*Duration.*—As a pot plant flowers last from 15 to 18 days. Petals fall cleanly away from plant.

*Size.*—Average flower diameter is 37 mm when open.

*Form.*—Shallow Cup.

*Shape of flower when viewed from the side.*—Upon opening, upper part: Flat. Upon opening, lower part: Flat. Open flower, upper part: Flattened Convex. Open flower, lower part: Concave.

*Petalage.*—Average range: 38 to 40 petals under normal conditions with 10 petaloids.

Color:

*Upon opening, petals.*—Outermost petals: Outer Side: Petal margins are Orange Group 26A to 26B. Orange Group 26B to 26C towards the central petal zone. Mid ridge bisecting the petal is Yellow Group 12B. Inner Side: Yellow-Orange Group 14D. Innermost petals: Outer Side: Petal margins are Orange Group 26A to 26B. Orange Group 26B to 26C towards the central petal zone. Mid ridge bisecting the petal is Yellow Group 12B. Inner ide: Yellow-Orange Group 14D.

*Upon opening, basal petal spots.*—Outermost petals: Outer Side: Yellow Group 12B. Inner Side: Yellow Group 12B. Innermost petals: Outer Side: Yellow Group 12B. Inner Side: Yellow Group 12B.

*After opening, petals.*—Outermost petals: Outer Side: Petal margins are Orange Group 26A to 26B. Orange Group 26B to 26C towards the central petal zone. Mid ridge bisecting the petal is Yellow Group 12B. Inner Side: Yellow-Orange Group 14D. Innermost petals: Outer Side: Petal margins are Orange Group 26A to 26B. Orange Group 26B to 26C towards the central petal zone. Mid ridge bisecting the petal is Yellow Group 12B. Inner Side: Yellow-Orange Group 14D.

*After opening, basal petal spots.*—Outermost petals: Outer Side: Yellow Group 12B. Inner Side: Yellow Group 12B. Innermost petals: Outer Side: Yellow Group 12B. Inner Side: Yellow Group 12B.

General tonality: On open flower Orange Group 28C with distinct intonations of Yellow Group 12B to Yellow-Orange Group 16D. No change in the general tonality at the end of the 10th day. Afterwards, general tonality is Yellow-Orange Group 16D to Orange Group 28D.

Petals:

*Petal reflex.*—Somewhat.

*Petal edge.*—Entire.

*Shape.*—Base Shape is acute. Apex Shape is round.

*Size.*—17 mm in length by 13 mm wide.

*Thickness.*—Thin.

*Arrangement.*—Not Formal.

Petaloids:

*Quantity.*—10.

*Size.*—15 mm long; 8 mm wide.

*Shape.*—Elliptical with strong undulations of margin.

*Color.*—Petaloid margins are Orange Group 26A to 26B. Orange Group 26B to 26C towards the central petal zone. Mid ridge bisecting the petal is Yellow Group 12B. Inner Side: Yellow-Orange Group 14D.

Reproductive organs:

*Pistils.*—Length: 4 mm long. Quantity: 30.

*Pollen.*—None Observed.

*Anthers.*—Size: 1 mm long. Color: Green-Yellow Group 1C. Quantity: 50.

*Filaments.*—Color: Yellow Group 13B. Length: 4 mm.

*Stigmas.*—Slightly superior in location to anthers. Color: Greyed-Yellow Group 162C.

*Styles.*—Color: Yellow-Green Group 150D.

*Seed formation.*—Not observed.

PLANT

Plant growth: Very compact, upright and bushy. When grown as a 8–11 cm pot plant, the average height of the plant itself is 20–40 cm and the average width is 30 cm.

Stems:

*Color.*—Young wood: Yellow-Green Group 144B. Older wood: Yellow-Green Group 146A.

*Internodal distance.*—15 mm.

*Length.*—8 cm.

*Surface texture.*—Young wood: Smooth. Older wood: Smooth.

Prickles:

*Incidence.*—14 per 10 cm of stem.

*Size.*—Average length: 4 mm.

*Color.*—On plants grown under high light conditions Greyed-Red Group 180A to 180B.

*Shape.*—Linear.

Plant foliage: Normal number of leaflets on normal leaves in middle of the stem: 7 leaflets.

*Compound leaf size.*—38 mm (l)×20 mm (w).

*Quantity.*—Very dense. 6 to 7 leaves per 10 cm of stem.

*Color.*—Mature Foliage: Upper Leaf Surface: Green Group 137A. Lower Leaf Surface: Green Group 138B. Juvenile Foliage: Upper Leaf Surface: Green Group 137A. Lower Leaf Surface: Green Group 138B.

Plant leaves and leaflets:

*Stipules.*—Size: 4 mm long by 2 mm wide. Shape: Linear with outward extending apecies. Color: Yellow Green Group 144A. Margins: Entire. Stipitate glands observed.

*Petiole.*—Length: 10 mm. Color: Yellow Green Group 146A. Underneath: Smooth. Margins: Stipitate Glands Observed. Anthocyanin: None-observed.

*Rachis.*—Size: 10 mm. Color: Green Group. Underneath: Smooth with few pricles. Margins: Few Stipitate Glands observed.

*Leaflet.*—Size: 14 mm in length by 8 mm wide. Edge: Finely serrated. General Shape: Elliptical. Apex Shape: Acute. Base Shape: Round. Texture: Smooth. Arrangement: Odd pinnate. Venation: Reticulate. Leaf Gloss: Matte.

Disease resistance: Average resistance to mildew, black spot, and Botrytis under normal growing conditions in Jackson County, Oreg., and Fredensborg, Denmark.

We claim:

1. A new and distinct variety of rose plant of the miniature class, substantially as herein illustrated and described as a distinct and novel rose variety due to its abundant, orange and orange blend flowers, vigorous growth, compact habit, suitability for production from softwood cuttings in pots, and durable flowers and foliage which make the variety suitable for distribution in the floral industry.

* * * * *

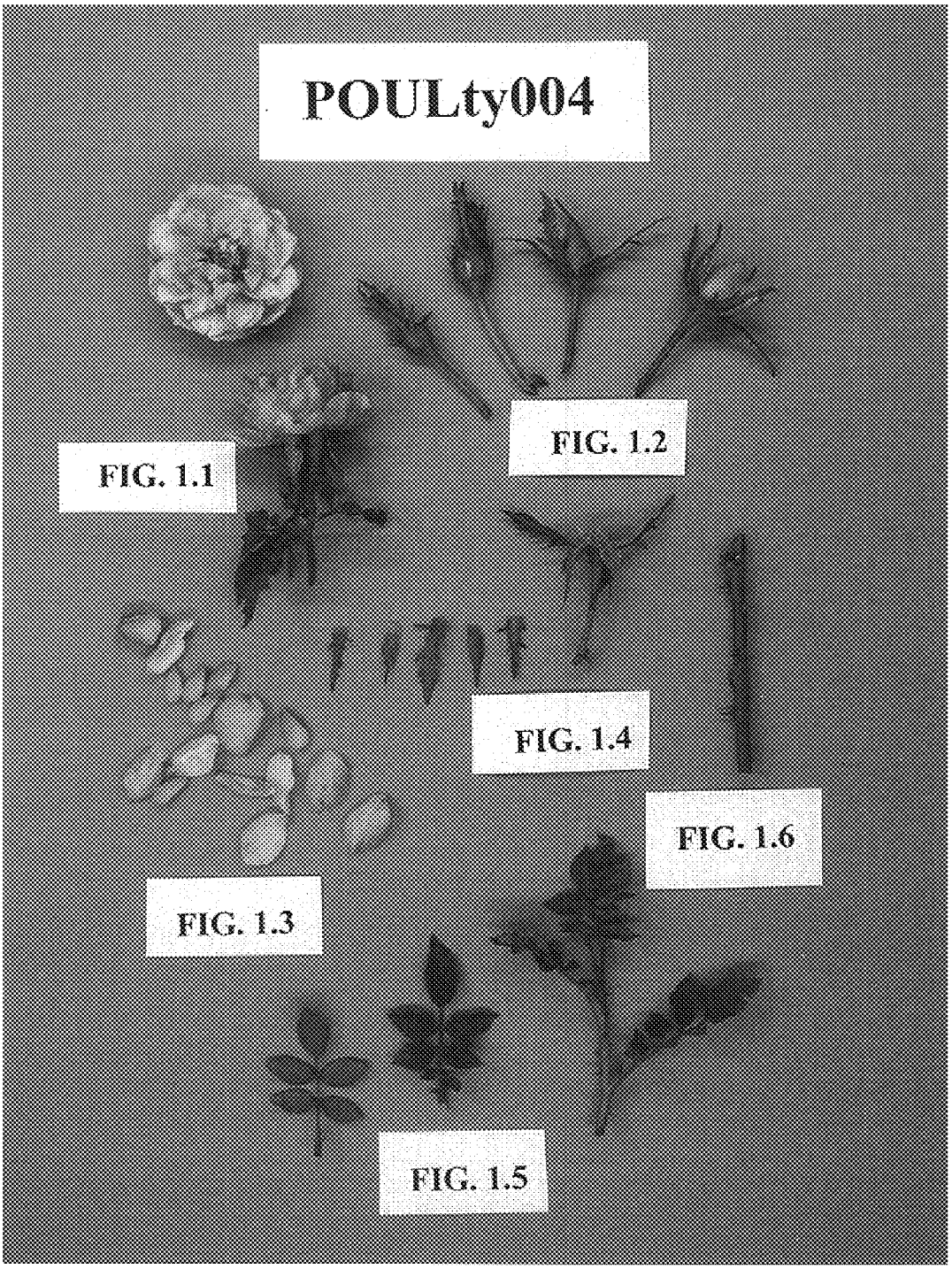
POULty004
FIG. 1.1
FIG. 1.2
FIG. 1.3
FIG. 1.4
FIG. 1.5
FIG. 1.6